[19] United States Patent
Sato et al.

[11] Patent Number: 5,004,846
[45] Date of Patent: Apr. 2, 1991

[54] PROCESS FOR PRODUCING NITROBENZENES

[75] Inventors: Hiroshi Sato; Kenichi Hirose; Koichi Nagai; Hiroshi Yoshioka; Yoshihiko Nagaoka, all of Ehime, Japan

[73] Assignee: Sumitomo Chemical Company, Ltd., Osaka, Japan

[21] Appl. No.: 352,022

[22] Filed: May 15, 1989

[30] Foreign Application Priority Data

May 18, 1988 [JP] Japan ................. 63-122671

[51] Int. Cl.$^5$ .............................................. C07C 79/10
[52] U.S. Cl. ...................................... 568/940; 568/927; 568/937; 568/939; 502/81; 502/84; 502/77
[58] Field of Search ............... 568/937, 939, 940, 727; 502/77, 81, 84; 585/466

[56] References Cited

U.S. PATENT DOCUMENTS

| | | | |
|---|---|---|---|
| 3,966,830 | 6/1976 | Shimada et al. | 568/937 |
| 4,112,006 | 9/1978 | Schubert et al. | 568/940 |
| 4,418,230 | 11/1983 | Bakke et al. | 568/940 |
| 4,426,543 | 1/1984 | Schumacher et al. | 568/940 |
| 4,551,568 | 11/1985 | Sato et al. | 568/939 |
| 4,600,702 | 7/1986 | Schumacher | 502/200 X |
| 4,618,733 | 10/1986 | Schumacher | 568/927 X |

*Primary Examiner*—Robert L. Stoll
*Assistant Examiner*—Chhaya Sayala
*Attorney, Agent, or Firm*—Cushman, Darby & Cushman

[57] ABSTRACT

Nitrobenzenes are prepared by nitrating benzenes in a vapor phase with dilute or concentrated nitric acid wherein the following (A) or (B) is used as a catalyst:

(A) acidic sheet clay minerals ion-exchanged with polyvalent metals, or (B) acidic composite oxides comprising oxides of metals belonging to Group IVA of the Mendeleefs' periodic table and tungsten oxide, molybdenum oxide, niobium oxide or zinc oxide.

These catalysts have high catalyst activity and selectivity for vapor phase nitration reaction of benzenes with nitric acid and besides the activity is retained for a long time.

10 Claims, No Drawings

PROCESS FOR PRODUCING NITROBENZENES

The present invention relates to a process for producing nitrobenzenes and more particularly to a process for producing nitrobenzenes by nitration of benzenes in vapor phase using nitric acid wherein specific sheet clay minerals or specific composite oxides are used as a catalyst.

Nitrobenzenes are important key industrial chemicals used as raw materials for dyes, medicines, agricultural chemicals, and the like.

One of economical production processes which is still popular is that proposed by E. Mitsherlich in 1834, namely, nitrating benzenes in a liquid phase with a mixture of concentrated nitric acid and concentrated sulfuric acid. This process requires so large amount of sulfuric acid that large quantities of waste sulfuric acid and waste water are incidentally produced. This is a severe problem from an industrial point of view. In order to solve the problem, a process is proposed where aromatic sulfonic acids supported on carriers are used in place of the concentrated sulfuric acid. (Japanese Patent Kokai Nos. 48-18239, 49-18833 and 50-4030). However, the process is a liquid phase one in nature and still suffers from the problems that a large amount of catalyst is needed and water by-produced causes deactivation of the catalyst. Accordingly, concentrated nitric acid of at least 90% or fuming nitric acid has to be used for the nitration, and furthermore the catalyst has to be subjected to azeotropic dehydration for reuse.

Another approach for nitration is that effected in a vapor phase. When nitration is conducted with nitric acid, there is a process where a silica-alumina catalyst is used as a catalyst (Japanese Patent Kokai No. 50-121234) or a process where a catalyst comprising inorganic acids such as sulfuric acid or phosphoric acid supported on carriers is used (Japanese Patent Kokai Nos. 50-126626, 50-126627, 51-63134 and 53-12823). Furthermore, when the nitration is conducted with $NO_2$, there are processes where the catalysts are a heteropoly-acid (Manuscripts for presentation of study on catalysts in meeting of the Catalyst Society, in 1985, page 80 (1985)), benzensulfonic acids supported on carriers or sulfonic acid group-containing organopolysiloxanes (Manuscripts for lecture on catalyst in the 60th meeting of the Catalyst Society, page 196, Sept. 25, 1987 and Journal of Organic Synthetic Chemical Associate, 45, 679 (1987)), composite oxides (Japanese Patent Kokai Nos. 58-162557 and 58-183644), zeolites (Japanese Patent Kokai Nos. 54-95521, 57-118539 and 58-157748) or niobium oxide (Japanese Patent Kokai No. 62-29556).

However, the former process where nitration is effected with nitric acid is low in space time yield of the objective product, namely, only about 0.04 kg/kg-catayst·h and low in yield based on the nitrating agent. Besides, life of the catalyst is short. On the other hand, the latter processes where nitration is effected with $NO_2$ are high in space time yield, but are not satisfactory yet in life of catalyst and yield based on the nitrating agent. Furthermore, troublesome processes are needed to recover and reoxidize NO by-produced in accordance with the following reaction formula (1), in order to increase the yield based on $NO_2$:

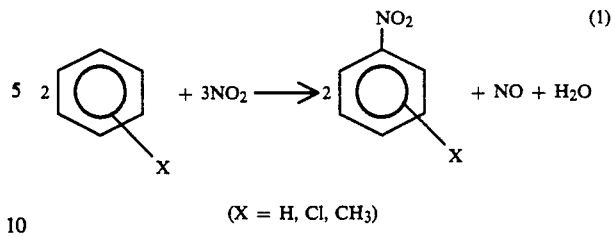

(X = H, Cl, $CH_3$)

The inventors have taken notice in that the nitration in a vapor phase with nitric acid as shown in the following formula (2) is superior, since there is no by-production of NO. After intensive researches are made, it has been found that specific sheet clay minerals and specific composite oxides exhibit very high catalyst activity and selectivity for the nitration of benzenes in vapor phase with nitric acid and this activity retains for a prolonged period. The present invention is based on this finding.

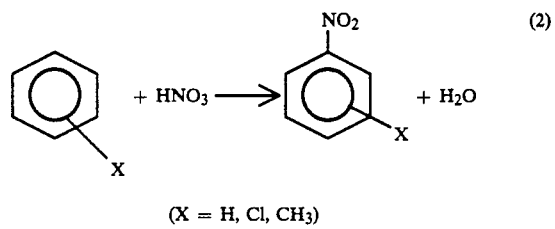

(X = H, Cl, $CH_3$)

According to the present invention, nitrobenzenes are produced by nitration of benzenes in vapor phase with nitric acid wherein (A) acidic sheet clay minerals which are ion-exchanged with polyvalent metal ions or (B) acidic composite oxides comprising oxides of elements of the Group IVA of the Mendeleefs' periodic table and tungsten oxide, molybdenum oxide, niobium oxide or zinc oxide are used as a catalyst.

The acidic sheet clay minerals which are ion-exchanged with polyvalent metal ions are sheet clay minerals, namely, minerals called philosilicates such as montmorilonite, saponite, hectorite, vermiculite, mica, fluorotetrasilicon mica and kaolinite (See "Mineral Chemistry II", pages 215–232, published from Kyoritsu Zensho in 1964) which are ion-exchanged with metal ions of divalent or higher.

Upon being ion-exchanged with polyvalent metal ions, these sheet clay minerals show acidity. These metal ions include ions of elements belonging to Groups IIA-VIIIA and IB-IVB of the Mendeleefs' periodic table such as ions of Al, Ga, Cu, Zn, Ni, Co, Fe, Ru, Mn, Re, Cr, Mo, W, V, Ti, Zr, lanthanoids, Mg and Ca.

The ion-exchanging is carried out by conventional methods, for example, by dispersing sheet clay minerals in aqueous solution of inorganic salts or organic salts of these metals and stirring the aqueous solution at a temperature from room temperature to boiling point for from several minutes to ten or longer hours, followed by filtering, washing and drying. The resulting minerals having an acid strength function $H_0$ of $+1.5$ or less are usually used. The resulting minerals are usually molded under pressure, ground to a given particle size and packed in a reaction tube for vapor phase nitration reaction.

Oxides of elements of Group IVA of the Mendeleefs' periodic table used in acidic composite oxides with tungsten oxide, molybdenum oxide, niobium oxide or zinc oxide are, for example, titanium oxide, zirconium oxide and hafnium oxide.

Composition of the composite oxides may be any combinations of the oxides selected from the above two groups. Examples are $TiO_2$-$MoO_3$, $TiO_2$-$WO_3$, $TiO_2$-$Nb_2O_5$, $TiO_2$-$ZnO$, $ZrO_2$-$MoO_3$, $ZrO_2$-$WO_3$, $ZrO_2$-$Nb_2O_5$, $ZrO_2$-$ZnO$, $HfO_2$-$MoO_3$, $HFO_2$-$WO_3$, $HfO_2$-$Nb_2O_5$ or $HfO_2$-$ZnO$. Especially preferred are $TiO_2$-$MoO_3$, $TiO_2$-$WO_3$, $ZrO_2$-$WO_3$, $TiO_2$-$Nb_2O_5$ or $TiO_2$-$ZnO$.

These composite oxides are prepared by various manners such as mentioned in text books and literatures, for example, "Metal Oxides and Composite Oxides" published from Kodansha Scientific in 1987. Some of the methods are co-precipitation where aqueous solution of salts of elements belonging to Group IVA of the Mendeleefs' periodic table is mixed with that of salts of tungsten, molybdenum, niobium or zinc, blending where oxides of one moiety are kneaded with oxides or hydroxides of another moiety or calcining where an aqueous solution of salts of one moiety is impregnated and concentrated in hydroxides of another moiety to obtain a precursor and then calcining is made at 200°-700° C. for several hours in an air stream.

The compositional ratio of the composite oxides used in the present invention is not critical, but usually the oxide has an acid strength $H_O$ of $+1.5$ or less, preferably $-3.0$ or less.

Benzenes which are starting materials include, for example, benzene, chlorobenzene or toluene. Nitric acid is used as a nitrating agent and concentration of nitric acid may be chosen in a wide range from concentrated nitric acid of 98% or higher to dilute nitric acid of 20–30%. It is one of the characteristics of the present invention that dilute nitric acid is usable and this brings about advantage not only in cost, but in materials of reaction instruments. Nitrobenzenes are obtained with high yield over a long period, even dilute nitric acid is used.

Nitration in a vapor phase is performed by feeding vapor of the starting benzene and vapor of nitric acid over catalysts. Usually, the vapors are diluted with an inert gas such as nitrogen, helium, argon or carbon dioxide.

Molar ratio of nitric acid and benzene is usually 5/1–1/10, preferably 2/1–1/5 and reaction temperature is usually 100–300° C., preferably 120°–200° C.

Time factor (W/F = (space velocity)$^{-1}$ of the starting materials are not critical and usually are selected from the range of 0.1–100 g-catalyst·h/mol.

The reaction is carried out in conventional apparatus for vapor phase flow reaction of fixed bed or fluidized bed and the product is washed with alkali and then recovered by distillation.

The following nonlimiting examples explain the present invention in more detail.

REFERENCE EXAMPLE 1

Aqueous aluminum nitrate solution (0.3 M, 100 ml) was added to montmorillonite (10 g, fine particle type; manufactured by Hayashi Kasei Co.), followed by stirring at about 70° C. for 2 hours. This procedure was repeated 4 times adding aqueous aluminum nitrate solution (0.3 M, 100 ml) afresh every cycle. The product was well washed with distilled water (2 liter) and dried at 120° C. overnight to obtain pale green powders. Acid strength observed by an indicator showed presence of a strong acid point of $H_O \leq <3.0$. This was molded under pressure and ground to obtain powders of 24–48 meshes in particle size. This was referred to as Catalyst No. 1.

EXAMPLE 1

Nitration was effected by feeding vapor of benzene and vapor of dilute nitric acid (60%) over the $Al^{3+}$ ion-exchanged montmorillonite catalyst (1.12g = 1.6ml) prepared in Reference Example 1 which had been packed in a conventional quartz tube in normal pressure fixed bed flowing system. Reaction conditions were as follows.

Reaction temperature = 150° C.
Partial pressure of benzene = 16.7 kPa
Partial pressure of $HNO_3$ = 8.68kPa
Carrier gas = $N_2$
Benzene/$HNO_3$$H_2O$/$N_2$ = 1/0.52/1.22/3.3 (in molar ratio)
Total feed = 138mmol/h
W/F = 8.1(g-cat·h/total feed mol)

The product was trapped at 0° C. and was analyzed by gas chromatography. Yield of nitrobenzene is shown by mol % based on nitric acid.

Results after 20 hours from the beginning of reaction are as shown below. Substantially no deterioration of catalyst activity was seen during this period.

Conversion of benzene = 47.9%
Yield of nitrobenzene (based on nitric acid) = 95.0%
Selectivity for nitrobenzene (based on benzene converted) $\geq$ 99.0%.
Space time yield (STY) = 1.26kg-NB/kg-cat·h (NB: nitrobenzene)

EXAMPLE 2

Example 1was repeated except that chlorobenzene was used in place of the benzene. The results are as follows.

Conversion of chlorobenzene = 45.4%
Yield of nitrochlorobenzenes (based on nitric acid) = 90.0%
Selectivity for nitrochlorobenzenes (based on chlorobenzene converted) $\geq$ 99.0%
Space time yield (STY) = 1.20kg/kg-cat·h
o/p ratio of nitrochlorobenzene = ½

REFERENCE EXAMPLE 2

Titanium tetraisopropoxide (42.6 g) was added dropwise to water (200 ml) to carry out hydrolysis and then thereto was added concentrated nitric acid (36.6 ml) to obtain homogeneous solution. Then, this solution was mixed with homogeneous solution comprising tungsten trioxide (11.6 g) and 28% aqueous ammonia (300 ml) to obtain precipitate.

The hydrogel produced by the co-precipitation method above was collected by filtration, washed with water, dried and then calcined in an air stream at 500° C. for 3 hours to obtain pale yellow composite oxide of $WO_3$-$TiO_2$ (23.6 g).

This oxide had an atomic ratio W/Ti of ⅛ and an acid strength $H_O$ of $-3.0$ or less by an indicator. This oxide was ground to 24–48 meshes in particle size. This was referred to as Catalyst No. 2.

EXAMPLE 3

The $WO_3$-$TiO_2$ composite oxide catalyst (1.12 g = 1.1 ml) prepared in Reference Example 2 was packed in an ordinary quartz reaction tube and pre-heated at 300° C. for 1 hour under a nitrogen stream. Then, vapor of benzene and vapor of 60% nitric acid were passed through the tube in a normal pressure fixed bed flowing system. Reaction conditions were the same as in Example 1. Results obtained after 20 hours from the beginning of the reaction are shown below. Substantially no deterioration of catalyst activity was seen during this period.

Conversion of benzene = 45.5%
Yield of nitrobenzene (based on nitric acid) = 90.0%
Selectivity for nitrobenzene (based on benzene converted) ≧ 99.0%
Space time yield (STY) = 1.20 kg-NB/kg-cat·h

EXAMPLE 4

Example 3 was repeated except that chlorobenzene was used in place of the benzene. The results are as follows.

Conversion of chlorobenzene = 41.6%
Yield of nitrochlorobenzene (based on nitric acid) = 82.4%
Selectivity for nitrochlorobenzene (based on chlorobenzene converted) ≧ 99.0%
Space time yield (STY) = 1.10 kg/kg-cat·h
p/o ratio of nitrochlorobenzene = 2.2

REFERENCE EXAMPLE 3

A solution comprising sodium tungstate (dehydrate, 24.8 g) and water (250 ml) was mixed with a solution comprising zirconium oxychloride (octahydrate, 12.1 g) and water (125 ml). To the mixture was added concentrated hydrochloric acid (125 ml) and the precipitate was aged. The precipitate was collected by filtration, washed with dilute hydrochloric acid, dried and then calcined at 450° C. for 7 hours in an air stream to obtain pale yellow $WO_3$-$ZrO_2$ composite oxide (21.5 g, an atomic ratio W/Zr = 2/1, and $H_O$ = −3.0 or less). The oxide was ground to the same particle size as in Reference Example 1. This was referred to as Catalyst No. 3.

EXAMPLE 5

Example 3 was repeated except that the $WO_3$-$ZrO_2$ composite oxide catalyst (1.12g = 1.2ml) prepared in Reference Example 3 was used in place of the $WO_3$-$TiO_2$ catalyst. The results obtained are shown below.

Conversion of benzene = 36.8%
Yield of nitrobenzene (based on nitric acid) = 72.9%
Selectivity for nitrobenzene (based on benzene converted) ≧ 99.0%
Space time yield (STY) = 0.96kg-NB/kg-cat·h

REFERENCE EXAMPLE 4

$Al^{3+}$ ion-exchanged bentonite catalyst was prepared in the same manner as in Reference Example 1 except that bentonite supplied by Nakarai Kagaku Co. was used in place of the montmorillonite. This catalyst was referred to as Catalyst No. 4.

REFERENCE EXAMPLE 5

Titanium tetrachloride (31 ml) was gradually added to ice-cooled water (60 ml) with stirring and dissolved therein. Then, to this solution was added dropwise homogeneous solution comprising water (500 ml), ammonium molybdate (12.3 g) and 28% aqueous ammonia (76 ml) with stirring to produce a precipitate. This precipitate was collected by filtration, washed with water, dried at 120° C. for one day, and calcined at 500° C. for 3 hours in an air stream to obtain black $Mo_3$-$TiO_2$ composite oxide powders (21.2 g). Elemental analysis of the product gave an atomic ratio Mo/Ti = ¼. This was referred to as Catalyst No. 5.

REFERENCE EXAMPLE 6

Titanium tetrachloride (31 ml) was gradually added to ice-cooled water (60 ml) and was dissolved therein. Then, to this solution was added dropwise homogeneous solution comprising water (600 ml), ammonium paratungstate (25.3 g) and 28% aqueous ammonia (65 ml) with stirring to produce a precipitate. This precipitate was collected by filtration, washed with water, dried at 120° C. for one day and calcined at 500° C. for 3 hours in an air stream to obtain yellow $WO_3$-$TiO_2$ composite oxide powders (31.0 g). Elemental analysis gave an atomic ratio W/Ti = ¼. This was referred to as Catalyst No. 6.

REFERENCE EXAMPLE 7

Titanium tetrachloride (35 ml) was gradually added to ice-cooled water (67 ml) with stirring and dissolved therein. Then, this solution was mixed with a solution comprising water (50 ml) and zinc chloride (14.8 g). To the resulting homogeneous solution was added dropwise 28% aqueous ammonia with stirring until pH reached 7 to produce a precipitate. This precipitate was collected by filtration, washed with water, dried at 120° C. for one day and calcined at 500° C. for 3 hours in an air stream to obtain white ZnO-$TiO_2$ composite oxide powders (26.3 g). Elemental analysis of the product gave an atomic ratio Zn/Ti = ¼. This was referred to as Catalyst No. 7.

EXAMPLES 6–13

Nitration of benzene with dilute nitric acid (70%) was carried out using 0.6 g each of Catalyst Nos. 4–7 prepared in Reference Examples 4–7. The reaction was carried out using an ordinary quartz reaction tube in a normal pressure fixed bed flowing system. Reaction conditions were acceleration conditions with increasing the feeding amount to catalyst as shown below.

Composition of feed (mmol/h):
Benzene/$HNO_3$/$H_2O$/$N_2$ = 40.0/20.0/30.0/110.0
Total feed = 200 mmol/h
W/F = 3.0 (g-cat·h/total feed (mol))
SV (space velocity) = 7,500 ml/g·h
Reaction temperature (furnace temperature) = 160° C. or 140° C.

The product was trapped at 0° C. and analyzed by gas chromatography. Results obtained after 2.5 hours from the beginning of the reaction are shown in Table 1. The results are shown based on nitric acid.

COMPARATIVE EXAMPLE 1

Example 6 was repeated except that heteropoly-acid supported on silica was used in place of Catalyst No. 4, said heteropoly-acid being proposed as catalyst for vapor phase nitration reaction using $NO_2$ as a nitrating agent (Manuscripts for presentation of study on catalyst in meeting of the Catalyst Society in 1985, page 80). The results obtained are shown in Table 1 based on nitric acid.

EXAMPLES 14 and 15

Nitration of benzene with dilute nitric acid (60%) was carried out continuously for a long time using Catalyst Nos. 1 and 2 prepared in Reference Examples 1 and 2. Reaction conditions were as shown below.

Composition of feed (mmol/h):

Benzene/$HNO_3$/$H_2O$/$N_2$=20.0/18.0/44.0/40.0
Total feed=122 mmol/h
Amount of catalyst=3.0 g
∴ W/F=24.6 (g-cat·h/total feed (mol))
∴ SV (space velocity)=900 ml/g·h
Reaction temperature (furnace temperature) =160° C.

The product was trapped at 0° C. and analyzed by gas chromatography. The results are shown in Table 2 based on nitric acid. Table 2 shows that activities of both catalysts somewhat decrease after the reaction of long time, but are restored to nearly the initial activities by calcination at 250° C. for 4 hours in air.

COMPARATIVE EXAMPLE 2

Example 14 was repeated except that, in place of the Catalyst No. 1, silica alumina catalyst was used which is proposed as a catalyst for vapor phase nitration reaction using nitric acid as a nitrating agent (Japanese Patent Kokai No. 50-121234). The results obtained are shown in Table 2 based on nitric acid.

COMPARATIVE EXAMPLE 3

Example 14 was repeated except that, in place of the Catalyst No. 1, tungsten oxide-molybdenum oxide composite oxide ($WO_3$/$MoO_3$=95/5) was used which is proposed as a catalyst for vapor phase nitration reaction using $NO_2$ as a nitrating agent (Japanese Patent Kokai No. 56-162557). The results obtained are shown in Table 2 based on nitric acid.

REFERENCE EXAMPLE 8

Montmorillonite (12.0 g) was dispersed in solution of zirconium oxychloride ($ZrCl_2 \cdot 8H_2O$, 128.9 g) in water (2 liter) and stirred for 1 hour at 65–70° C. A precipitate was filtered, washed, dried at 120° C. for 6 hours and calcined at 400° C. for 4 hours in an air stream to prepare a Zr-crosslinked montmorillonite catalyst. This was referred to as Catalyst No. 8.

REFERENCE EXAMPLES 9–11

Montmorillonite catalysts ion-exchanged with $Fe^{3+}$, $Cr^{3+}$, and $Bi^{3+}$, respectively were prepared by carrying out ion-exchange of montmorillonite in the same manner as in Reference Example 1 except that 0.3M aqueous solution of iron nitrate, chromium nitrate or bismuth nitrate was used in place of the 0.3M aluminum nitrate. These catalysts were referred to as Catalyst Nos. 9, 10 and 1, respectively.

EXAMPLES 16–19

Example 6 was repeated except that Catalyst Nos. 8-11 (0.6 g each) prepared in Reference Examples 8-11 were used in place of the Catalyst No. 4, respectively.
The results obtained are shown in Table 3 based on nitric acid.

EXAMPLE 20

Nitration of toluene was carried out with dilute nitric acid (70%) using 3.0 g of Catalyst No. 4( $Al^{3+}$+bentonite) prepared in Reference Example 4. Reaction conditions were as follows.
Composition, of feed (mmol/h):
Toluene/$HNO_3$/$H_2O$/$N_2$=40.0/20.0/30.0/110/0
Total feed=200 mmol/h
∴ W/F=15.0 (g-cat·h/total feed (mol))
∴ SV (space velocity)=1,500 ml/g·h
Reaction temperature (furnace temperature) =160° C.

Results obtained after 2.5 hours from the beginning of the reaction are shown below based on nitric acid.
Conversion of nitric acid=41.7%
Yield of nitrotoluene=25.0%
p/o/m ratio of nitrotoluene=1.3/1.0/0.09

TABLE 1

| Example No. | Catalyst No. | Catalyst Composition | Reaction temperature (°C.) | $HNO_3$ conversion (%) | NB yield (%) | NB selectivity (%) | NB-STY kg-NB/kg-cat.-h |
|---|---|---|---|---|---|---|---|
| 6 | 4 | $Al^{3+}$ Mont | 160 | 93.4 | 91.4 | 97.8 | 3.61 |
| 7 | 4 | $Al^{3+}$ Mont | 140 | 87.9 | 86.6 | 98.6 | 3.42 |
| 8 | 5 | Mo-Ti | 160 | 83.4 | 80.7 | 96.8 | 3.11 |
| 9 | 5 | Mo-Ti | 140 | 64.6 | 63.1 | 97.6 | 2.43 |
| 10 | 6 | W-Ti | 160 | 64.3 | 62.1 | 96.6 | 2.39 |
| 11 | 6 | W-Ti | 140 | 48.5 | 47.8 | 98.6 | 1.84 |
| 12 | 7 | Zn-Ti | 160 | 69.1 | 65.1 | 94.2 | 2.50 |
| 13 | 7 | Zn-Ti | 140 | 54.6 | 53.6 | 98.1 | 2.06 |
| Comparative Example 1 | | P-W/$SiO_2$[1] | 160 | 15.4 | 15.3 | 99.1 | 0.60 |

NB; nitrobenzene, STY; space time yield, $Al^{3+}$ Mont; $Al^{3+}$ ion-exchanged montmorillonite
Note[1] 82 wt % $H_3PW_{12}O_{40}$/$SiO_2$

TABLE 2

| Example No. | Run No. | Catalyst No. | Catalyst Composition | Reaction time (day) | $HNO_3$ conversion (%) | NB yield (%) | NB selectivity (%) | NB-STY kg-NB/kg-cat.-h |
|---|---|---|---|---|---|---|---|---|
| 14 | 1 | 1 | $Al^{3+}$ Mont | 1 | 92.4 | 87.5 | 94.7 | 0.64 |
|  | 2 | 1 | $Al^{3+}$ Mont | 20 | 83.0 | 80.3 | 96.8 | 0.59 |
|  | 3 |  | Regenerated $Al^{3+}$ Mont[1] | 1 | 92.0 | 87.2 | 94.8 | 0.64 |
| 15 | 1 | 2 | W-Ti | 1 | 84.6 | 79.2 | 93.6 | 0.58 |
|  | 2 | 2 | W-Ti | 22 | 81.2 | 77.1 | 94.9 | 0.57 |
|  | 3 |  | Regenerated W-Ti[1] | 1 | 84.3 | 79.0 | 93.7 | 0.58 |
| Comparative | 1 |  | $SiO_2$-$Al_2O_3$[2] | 1 | 47.2 | 46.0 | 97.5 | 0.34 |

TABLE 2-continued

| Example No. | Run No. | Catalyst No. | Catalyst Composition | Reaction time (day) | HNO$_3$ conversion (%) | NB yield (%) | NB selectivity (%) | NB-STY kg-NB/kg-cat.-h |
|---|---|---|---|---|---|---|---|---|
| tive Example 2 | 2 | | SiO$_2$-Al$_2$O$_3$[2] | 10 | 33.0 | 32.3 | 98.0 | 0.24 |
| Comparative Example 3 | 1 | | W-Mo | 1 | 12.0 | 11.5 | 95.8 | 0.08 |

NB; nitrobenzene, STY; space time yield, Al$^{3+}$ Mont; Al$^{3+}$ ion-exchanged montmorillonite
Note[1] After regeneration treatment in air stream at 250° C. for 4 hours.
Note[2] Silica alumina N631-H manufactured by Nikki Co.

TABLE 3

| Example No. | Catalyst No. | Catalyst Composition | Reaction temperature (°C.) | HNO$_3$ conversion (%) | NB yield (%) | NB selectivity (%) | NB-STY kg-NB/kg-cat.-h |
|---|---|---|---|---|---|---|---|
| 16 | 8 | Zr$^{4+}$ Mont | 160 | 92.6 | 89.1 | 96.3 | 3.52 |
| 17 | 9 | Fe$^{3+}$ Mont | 160 | 92.1 | 90.0 | 97.7 | 3.55 |
| 18 | 10 | Cr$^{3+}$ Mont | 160 | 77.9 | 76.4 | 98.1 | 3.02 |
| 19 | 11 | Bi$^{3+}$ Mont | 160 | 76.9 | 75.5 | 98.1 | 2.98 |

NB; nitrobenzene, STY; space time yield, Zr$^{4+}$ Mont; Zr$^{4+}$ crosslinked montmorillonite Fe$^{3+}$ Mont, Cr$^{3+}$ Mont, Bi$^{3+}$ Mont; Bi$^{3+}$ Mont; Fe$^{3+}$, Cr$^{3+}$, Bi$^{3+}$ ion-exchanged montmorillonites, respectively

We claim:

1. A process for producing nitrobenzenes which comprises nitrating benzenes in a vapor phase using nitric acid as a nitrating agent in the presence of acidic sheet clay minerals which are sheet clay minerals ion-exchanged with a member of the group selected from Al$^{3+}$, Ti$^{4+}$, Zr$^{4+}$, Fe$^{3+}$, Cr$^{3+}$, Bi$^{3+}$ and La$^{3+}$.

2. A process according to claim 1, wherein the acidic sheet clay minerals are montmorillonite which are ion-exchanged with Al$^{3+}$, Ti$^{4+}$, Zr$^{4+}$, Fe$^{3+}$, Cr$^{3+}$, Bi$^{3+}$, or La$^{3+}$.

3. A process according to claim 1, wherein the benzenes are benzene, chlorobenzene or toluene.

4. A process according to claim 1, wherein the nitric acid is dilute nitric acid.

5. A process according to claim 1, wherein the acidic sheet clay minerals have an acid strength H$_O$ of +1.5 or less.

6. A process for producing nitrobenzenes which comprises nitrating benzenes in a vapor phase using nitric acid as a nitrating agent in the presence of acidic composite oxides comprising oxides of metals belonging to Group IVA of Medeleefs' periodic Table and tungsten oxide, molybdenum oxide, niobium oxide or zinc oxide.

7. A process according to claim 6, wherein the benzenes are benzene, chlorobenzene or toluene.

8. A process according to claim 6, wherein the nitric acid is dilute nitric acid.

9. A process according to claim 6, wherein the acidic composite oxides are TiO$_2$-MoO$_3$, TiO$_2$-WO$_3$, TiO$_2$-ZnO or ZrO$_2$-WO$_3$.

10. A process according to claim 6, wherein the acidic composite oxides have an acid strength H$_O$ of +1.5 or less.

* * * * *